US00PP28501P3

(12) United States Plant Patent
Olesen

(10) Patent No.: US PP28,501 P3
(45) Date of Patent: Oct. 10, 2017

(54) MINIATURE ROSE PLANT NAMED 'POULPAR087'

(50) Latin Name: ***Rosa* hybrid**
Varietal Denomination: Poulpar087

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 28 days.

(21) Appl. No.: 14/756,258

(22) Filed: Aug. 20, 2015

(65) Prior Publication Data

US 2017/0055389 P1 Feb. 23, 2017

(51) Int. Cl.
*A01H 5/02* (2006.01)

(52) U.S. Cl.
USPC ..... Plt./121

(58) Field of Classification Search
USPC ..... Plt./121
See application file for complete search history.

(56) References Cited

PUBLICATIONS

PLUTO Plant Variety Database Aug. 2, 2016. p. 1.*
Party Perfection by Poulsen Outdoor Main Varieties 2013.*

* cited by examiner

*Primary Examiner* — Annette Para

(57) ABSTRACT

A new garden rose plant of the Miniature class which has abundant, pink flowers and attractive foliage. This new and distinct variety has shown to be uniform and stable in the resulting generations from asexual propagation.

3 Drawing Sheets

Botanical designation: *Rosa* hybrid.
Variety denomination: 'Poulpar087'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2008 and the resulting seeds were planted in a controlled environment in Fredensborg, Denmark. The new variety, named 'Poulpar087', originated as a single seedling from the stated cross.

The new variety may be distinguished from its male pollen parent and female seed parent primarily by the following characteristics. The female seed parent has orange pink blend flowers, while the new variety has pink flowers. The male pollen parent has flowers which are russet in color.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpar087' from all other varieties of which we are aware.

As part of the rose development program, Mogens N. Olesen germinated the seeds from the aforementioned hybridization during winter of 2008 and conducted evaluations on the resulting seedlings in a controlled environment in Fredensborg, Denmark. 'Poulpar087' was selected in the spring of 2009 by the inventor as a single plant from the progeny of the aforementioned hybridization.

Asexual reproduction of 'Poulpar087' by traditional budding and rooted cuttings was first done by Mogens N. Olesen in the nursery in Fredensborg, Denmark in July, 2009. This initial and other subsequent asexual propagations conducted in controlled environments have demonstrated that the characteristics of 'Poulpar087' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar087'.

Specifically illustrated are open flowers, flower petals detached, sepals detached, leaves, and bare stems. Plants shown are 1 year old.

DETAILED DESCRIPTION OF THE VARIETY

Figure 1:
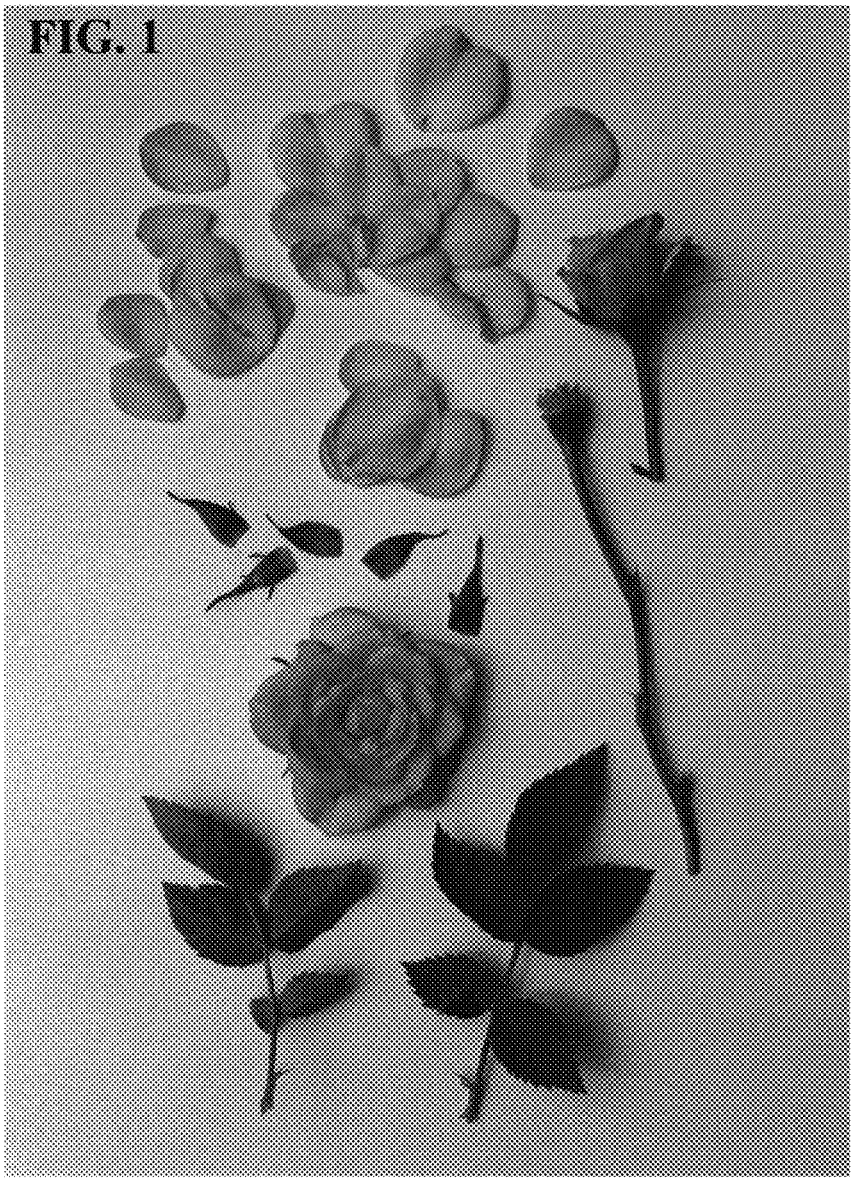
Figure 2:
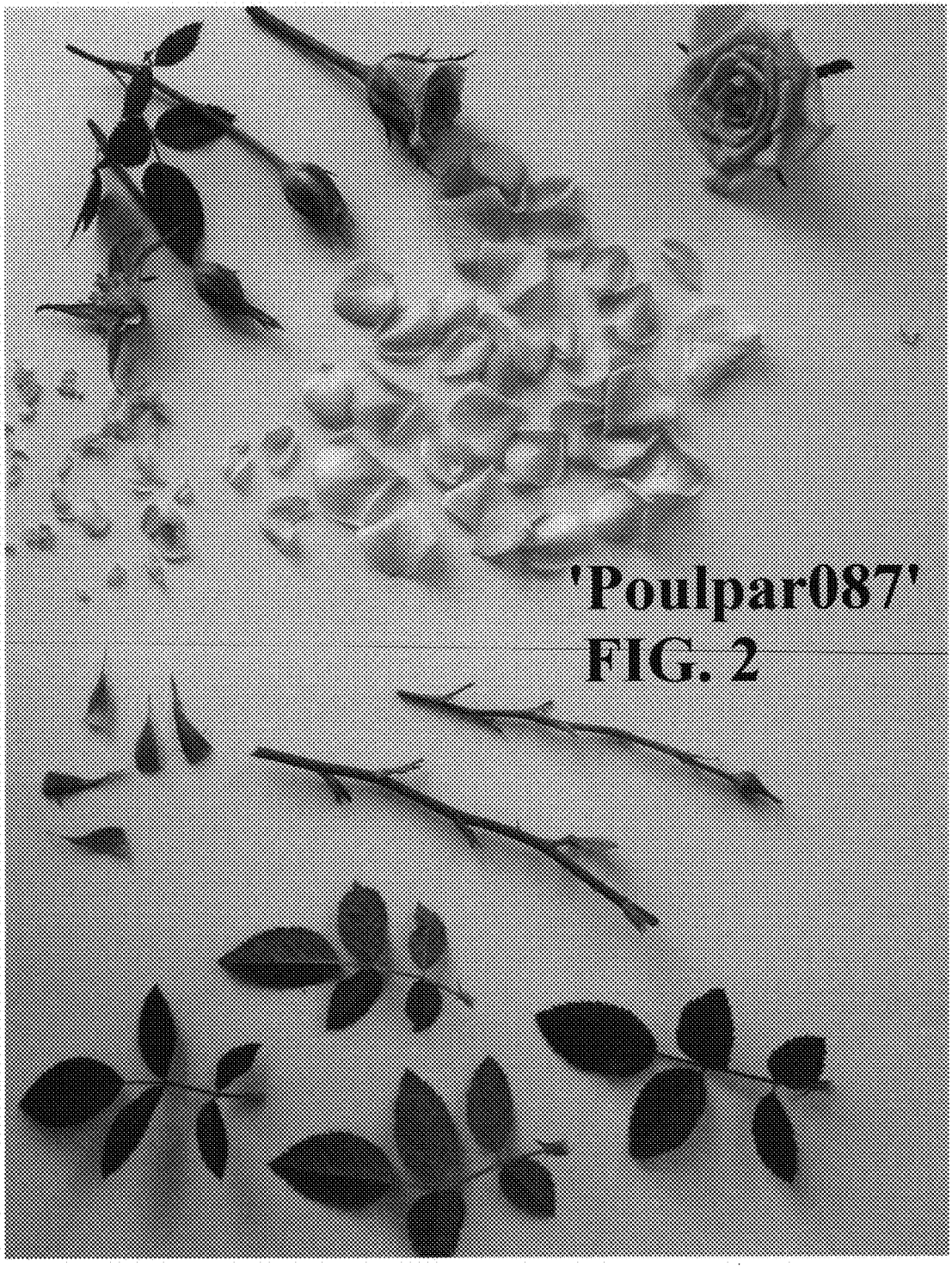
Figure 3:
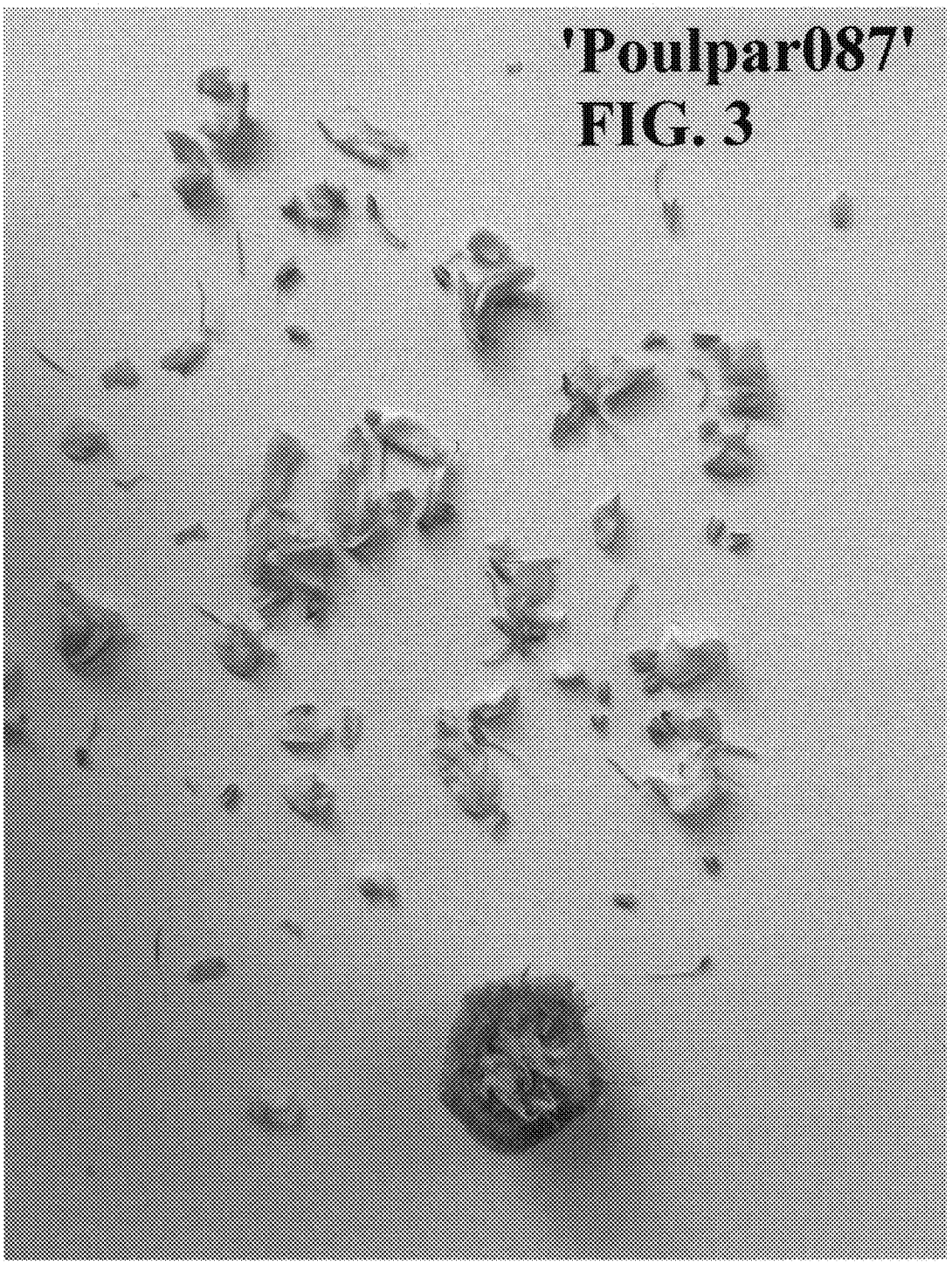

The following is a description of 'Poulpar087', as observed in its growth in in a field nursery in Marion County, Oreg. Observed plants are 1 year old, and were grown on their own roots. Color references are made using The Royal Horticultural Society (London, England) Colour Chart, 2001, except where common terms of color are used.

For a comparison, several physical characteristics of the rose variety 'Poulra024', U.S. Plant Pat. No. 15,017 are compared to 'Poulpar087' in Chart 1.

CHART 1

| | 'Poulpar087' | 'Poulra024' |
|---|---|---|
| Petal Count | 80 | 20 to 40 |
| Flower Diameter | 50 mm | 45 to 50 mm |
| General Tonality of Flower Color | Red Group 49A | Red Group 52C |

Flower and Flower Bud

Blooming habit: Continuous.

Flower bud:

*Size.*—Upon opening, 27 mm in length from base of receptacle to end of bud. Bud diameter is 12 mm.

*Bud form.*—Ovoid.

*Bud color.*—As sepals divide petals are Red Group 49A.

*Sepal inner surface.*—Color: Green Group 38B. Surface: Lightly pubescent.

*Sepal outer surface.*—Color: Yellow-Green Group 144A with intonations of Greyed-Red Group 180B. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—20 mm long, 8 mm wide.

*Receptacle.*—Texture: Smooth. Size: 4 mm in height, 10 mm wide. Color: Yellow-Green Group 144B. Shape: Campanulate.

*Pedicel.*—Surface: Broad funnel. Length: About 40 mm. Diameter: 2.5 mm on average. Color: Yellow-Green Group 144B. Strength: Moderate.

Flower bud development: Flower buds are borne singly.

Flower bloom:

*Fragrance.*—None.

*Duration.*—The blooms have a duration on the plant of approximately 20 days. Petals do not fall cleanly away from plant after flowers have fully matured.

*Size.*—Flower diameter is 50 mm when open. Flower depth is 20 mm.

*Flower shape.*—Rosette very double flower with many slightly overlapping petals of different sizes.

*Shape of flower, side view.*—The upper and lower portion is flat.

Petalage: Under normal conditions, flowers have 80 petals total.

General tonality of flower: Open flowers are Red Group 49A.

Petal color:

*Upon opening, outer petals.*—Upper surface: Red Group 49B at the margin and middle zone blending with Yellow Group 7B at the basal zone. Lower surface: Red Group 49B at the margin and middle zone blending with Yellow Group 7B at the basal zone.

*Upon opening, inner petals.*—Upper surface: Red Group 49A at the marginal and middle zone blending with Yellow Group 7B at the basal zone. Lower surface: Red Group 49A at the marginal and middle zone blending with Yellow Group 7B at the basal zone.

*After opening, outer and inner petals.*—Upper surface: Red Group 49C at the marginal and middle zone blending with Yellow Group 10B at the basal zone. Lower surface: Red Group 49C at the marginal and middle zone blending with Yellow Group 10C at the basal zone.

Petals:

*Petal reflex.*—Outer petals have strong reflex.

*Margin.*—Entire and uniform. Occasionally there is a point at the apex. No undulations.

*Shape.*—Broad elliptic. Apex shape: Rounded. Base shape: Obtuse.

*Size.*—25 mm (l)×20 to 25 mm (w).

*Texture.*—Smooth.

*Thickness.*—Average.

Petaloids:

*Size.*—About 8 mm (l) by 4 mm (w).

*Quantity.*—About 25 petaloids.

*Shape.*—Acute base and apex.

*Color.*—Red Group 49A at the marginal and middle zone blending with Yellow Group 7B at the basal zone.

Reproductive flower parts:

*Pollen.*—None observed.

*Anthers.*—Size: 1 mm in length. Color: Orange Group 24B. Quantity: 30 on average.

*Filaments.*—Color: Yellow Group 7B. Length: 3 mm.

*Pistils.*—Length: 4 mm. Quantity: 20 on average.

*Stigmas.*—Color: Yellow Group 7D.

*Styles.*—Color: Red Group 24A.

*Location of stigmas.*—Level in location relative to the length of the filaments and the height of the anthers.

*Hips.*—None Observed.

Plant

Plant growth: Upright, bushy. Plants are about 35 cm in height, and 30 cm wide.

Stems:

*Color.*—Juvenile growth: Yellow-Green Group 144B. Mature growth: Yellow-Green Group 146B.

*Length.*—On average, canes are 30 cm from the base of the plant to the flowering portion.

*Diameter.*—3 mm.

*Internodes.*—On mature canes about 20 mm between nodes.

*Surface texture.*—Young wood: Smooth. Older wood: Smooth.

Long prickles:

*Incidence.*—About 4 prickles per 10 cm of stem.

*Size.*—Average length of prickles on mature stems is 3 mm.

*Shape.*—Upper and lower portion are deep concave.

*Color.*—Juvenile prickles: Yellow-Green Group 145A. Mature prickles: Yellow-Green Group 145A.

Plant foliage:

*Compound leaf.*—85 mm (l)×65 (w).

*Quantity.*—4 leaves per 10 cm of stem on average.

*Leaf bearing angle to the stem.*—60 degrees.

*Color of juvenile foliage.*—Upper side: Yellow-Green Group 147B. Lower side: Yellow-Green Group 148B. Anthocyanin: Greyed-Purple Group 183B.

*Color of mature foliage.*—Upper side: Yellow-Green Group 147A. Lower side: Yellow-Green Group 147B.

Plant leaves and leaflets:

*Stipules.*—Size: 8 mm long, 4 mm wide. Quantity: 2 per compound leaf. Shape: Linear, slightly broad based with outward extending apices. Margins: Finely serrated. Color: Yellow-Green Group 146B.

*Petiole*.—Length: About 9 mm. Diameter: 1 mm.

*Upper surface*.—Color: Yellow-Green Group 146B.

*Lower surface*.—Color: Yellow-Green Group 144A.

*Rachis*.—Length: 15 to 20 mm. Upper surface: Color: Yellow-Green Group 146B.

*Lower surface*.—Color: Yellow-Green Group 144A.

*Leaflet*.—Quantity: Normally 5 leaflets. Margins: Serrated. Size: On average terminal leaflets are about 40 mm long, 20 mm wide. Shape: Generally elliptical. Base: Rounded. Apex: Mucronate. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the miniature rose class named 'Poulpar087', substantially as illustrated and described herein, due to its abundant pink flowers, disease resistance, and extended period of bloom.

* * * * *

'Poulpar087'

'Poulpar087'